(12) United States Patent
Lafontaine (10) Patent No.: US 7,942,897 B2
(45) Date of Patent: May 17, 2011

(54) SYSTEM FOR CLOSING AN OPENING IN A BODY CAVITY

(75) Inventor: Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 975 days.

(21) Appl. No.: 10/616,622

(22) Filed: Jul. 10, 2003

(65) Prior Publication Data

US 2005/0010248 A1    Jan. 13, 2005

(51) Int. Cl.
*A61D 1/00* (2006.01)
(52) U.S. Cl. .......................... 606/213; 606/139; 606/157
(58) Field of Classification Search .......... 606/213–214, 606/139, 148–149, 143–144, 151, 157–158, 606/193
See application file for complete search history.

(56) References Cited

U.S. PATENT DOCUMENTS

| | | | |
|---|---|---|---|
| 3,438,374 A | 4/1969 | Falb et al | 128/334 |
| 4,002,173 A | 1/1977 | Manning et al. | 128/296 |
| 4,068,655 A | 1/1978 | LeRoy | 128/20 |
| 4,140,537 A | 2/1979 | Luck et al. | 106/155 |
| 4,292,972 A | 10/1981 | Pawelchak et al. | 128/296 |
| 4,365,621 A | 12/1982 | Brundin | 128/1 |
| 4,372,314 A | 2/1983 | Wall | 128/296 |
| 4,390,519 A | 6/1983 | Sawyer | 424/28 |
| 4,404,970 A | 9/1983 | Sawyer | 128/325 |
| 4,405,324 A | 9/1983 | Cruz, Jr. | 604/376 |
| 4,424,208 A | 1/1984 | Wallace et al. | 424/177 |
| 4,509,504 A | 4/1985 | Brundin | 128/1 |
| 4,515,637 A | 5/1985 | Cioca | 424/94 |
| 4,543,410 A | 9/1985 | Cruz, Jr. | 536/84 |
| 4,582,640 A | 4/1986 | Smestad et al. | 260/123 |
| RE32,208 E | 7/1986 | Mattei et al. | 424/78 |
| 4,597,960 A | 7/1986 | Cohen | 424/28 |
| 4,703,108 A | 10/1987 | Silver et al. | 530/356 |
| 4,744,364 A | 5/1988 | Kensey | 128/334 |
| 4,749,689 A | 6/1988 | Miyata et al. | 514/21 |
| 4,852,568 A | 8/1989 | Kensey | 128/325 |
| 4,890,612 A | 1/1990 | Kensey | 606/213 |

(Continued)

FOREIGN PATENT DOCUMENTS

EP        0 044 624 A1    1/1982

(Continued)

OTHER PUBLICATIONS

Partial International Search Report PCT/US2004/021972; report dated Dec. 6, 2004.

(Continued)

*Primary Examiner* — Todd E Manahan
*Assistant Examiner* — Diane Yabut
(74) *Attorney, Agent, or Firm* — Seager, Tufte & Wickhem, LLC (57) ABSTRACT

A closure device closes an opening in a body cavity. The closure device includes an elongate delivery member and a closure component which is removably connected to the distal end of the delivery member. The closure component has a collapsible backing movable between a non-collapsed position and a collapsed position. The closure component also includes a plurality of fibrous tissue engaging members disposed on the backing and oriented in a non-engaging orientation when traveling in a distal direction and in an engaging orientation when traveling in a proximal direction. The fibrous tissue engaging members become entangled in the backing when the backing is in the collapsed position.

36 Claims, 4 Drawing Sheets

U.S. PATENT DOCUMENTS

| | | | |
|---|---|---|---|
| 4,979,947 A | 12/1990 | Berman | 604/369 |
| 5,021,059 A | 6/1991 | Kensey et al. | 606/213 |
| 5,061,274 A | 10/1991 | Kensey | 606/213 |
| 5,100,429 A | 3/1992 | Sinofsky et al. | 606/195 |
| 5,108,421 A | 4/1992 | Fowler | 606/213 |
| 5,192,300 A | 3/1993 | Fowler | 606/213 |
| 5,192,302 A * | 3/1993 | Kensey et al. | 606/213 |
| 5,254,105 A | 10/1993 | Haaga | 604/265 |
| 5,254,133 A | 10/1993 | Seid | |
| 5,290,310 A | 3/1994 | Makower et al. | 606/213 |
| 5,292,309 A | 3/1994 | Van Tassel et al. | 604/117 |
| 5,292,332 A | 3/1994 | Lee | 606/213 |
| 5,310,407 A | 5/1994 | Casale | 604/51 |
| 5,320,639 A | 6/1994 | Rudnick | 606/213 |
| 5,324,306 A | 6/1994 | Makower et al. | 606/213 |
| 5,330,445 A | 7/1994 | Haaga | 604/265 |
| 5,334,216 A | 8/1994 | Vidal et al. | 606/213 |
| 5,376,376 A | 12/1994 | Li | 424/443 |
| 5,383,891 A | 1/1995 | Walker | 606/196 |
| 5,383,897 A | 1/1995 | Wholey | |
| RE34,866 E | 2/1995 | Kensey et al. | 606/213 |
| 5,391,183 A | 2/1995 | Janzen et al. | 606/213 |
| 5,431,639 A | 7/1995 | Shaw | 604/264 |
| 5,449,375 A | 9/1995 | Vidal et al. | 606/213 |
| 5,456,693 A * | 10/1995 | Conston et al. | 606/192 |
| 5,460,621 A | 10/1995 | Gertzman et al. | 604/358 |
| 5,486,195 A | 1/1996 | Myers et al. | 606/213 |
| 5,522,840 A | 6/1996 | Krajicek | 606/213 |
| 5,540,715 A | 7/1996 | Katsaros et al. | 606/213 |
| 5,569,297 A | 10/1996 | Makower et al. | 606/201 |
| 5,591,205 A | 1/1997 | Fowler | 606/213 |
| 5,603,698 A | 2/1997 | Roberts et al. | 604/104 |
| 5,624,669 A | 4/1997 | Leung et al. | 424/78.35 |
| 5,643,318 A | 7/1997 | Tsukernik et al. | 606/214 |
| 5,643,596 A | 7/1997 | Pruss et al. | 424/426 |
| 5,645,849 A | 7/1997 | Pruss et al. | 424/426 |
| 5,683,418 A * | 11/1997 | Luscombe et al. | 606/232 |
| 5,690,674 A | 11/1997 | Diaz | 606/213 |
| 5,702,413 A | 12/1997 | Lafontaine | 606/159 |
| 5,723,005 A * | 3/1998 | Herrick | 623/4.1 |
| 5,728,132 A | 3/1998 | Van Tassel et al. | 606/213 |
| 5,782,860 A | 7/1998 | Epstein et al. | 606/213 |
| 5,782,861 A | 7/1998 | Cragg et al. | 606/216 |
| 5,823,198 A | 10/1998 | Jones et al. | 128/899 |
| 5,846,251 A * | 12/1998 | Hart | 606/127 |
| 5,868,762 A | 2/1999 | Cragg et al. | 606/144 |
| 5,895,412 A | 4/1999 | Tucker | 606/215 |
| 5,906,631 A | 5/1999 | Imran | 606/213 |
| 5,964,782 A * | 10/1999 | Lafontaine et al. | 606/213 |
| RE36,370 E | 11/1999 | Li | 424/443 |
| 5,984,950 A | 11/1999 | Cragg et al. | 606/216 |
| 6,071,300 A | 6/2000 | Brenneman et al. | 606/213 |
| 6,071,301 A | 6/2000 | Cragg et al. | 606/213 |
| 6,086,607 A | 7/2000 | Cragg et al. | 606/213 |
| 6,162,192 A | 12/2000 | Cragg et al. | 604/15 |
| 6,162,240 A | 12/2000 | Cates et al. | 606/213 |
| 6,183,496 B1 | 2/2001 | Urbanski | 606/213 |
| 6,183,497 B1 | 2/2001 | Sing et al. | 606/213 |
| 6,183,498 B1 | 2/2001 | Devore et al. | 606/214 |
| 6,200,328 B1 | 3/2001 | Cragg et al. | 606/213 |
| 6,261,309 B1 * | 7/2001 | Urbanski | 606/213 |
| 6,267,761 B1 | 7/2001 | Ryan | 606/50 |
| 6,270,464 B1 | 8/2001 | Fulton, III et al. | 600/562 |
| 6,270,515 B1 * | 8/2001 | Linden et al. | 606/213 |
| 6,296,657 B1 | 10/2001 | Brucker | 606/213 |
| 6,299,619 B1 | 10/2001 | Greene, Jr. et al. | 606/108 |
| 6,312,446 B1 * | 11/2001 | Huebsch et al. | 606/213 |
| 6,315,753 B1 | 11/2001 | Cragg et al. | 604/15 |
| 6,334,865 B1 * | 1/2002 | Redmond et al. | 606/213 |
| 6,350,274 B1 | 2/2002 | Li | 606/213 |
| 6,440,151 B1 | 8/2002 | Cragg et al. | 606/213 |
| 6,440,153 B2 | 8/2002 | Cragg et al. | 606/213 |
| 6,447,534 B2 | 9/2002 | Cragg et al. | 606/213 |
| 6,500,152 B1 | 12/2002 | Illi | 604/164.07 |
| 6,500,190 B2 | 12/2002 | Greene, Jr. et al. | 606/191 |
| 6,537,300 B2 * | 3/2003 | Girton | 606/213 |
| 6,554,851 B1 | 4/2003 | Palasis et al. | 606/213 |
| 2002/0010150 A1 | 1/2002 | Cortese et al. | 514/54 |
| 2002/0025921 A1 | 2/2002 | Petito et al. | 514/2 |
| 2002/0077657 A1 | 6/2002 | Ginn et al. | 606/213 |
| 2003/0013989 A1 | 1/2003 | Obermiller et al. | 600/567 |

FOREIGN PATENT DOCUMENTS

| | | |
|---|---|---|
| EP | 0 145 970 A2 | 11/1983 |
| EP | 0 044 624 B1 | 10/1984 |
| EP | 0467516 A1 | 1/1992 |
| EP | 0 891 193 B1 | 4/1997 |
| EP | 0 726 749 A2 | 1/2000 |
| EP | 1 269 951 A1 | 1/2003 |
| JP | 55116736 A | 9/1980 |
| JP | 62004232 A | 1/1987 |
| JP | 63070507 A | 4/1988 |
| JP | 02182259 A | 7/1990 |
| JP | 05163157 A | 6/1993 |
| JP | 09294765 A | 11/1997 |
| JP | 2002143210 A | 5/2002 |
| RU | 2122867 C1 | 12/1998 |
| RU | 2135105 C1 | 8/1999 |
| RU | 2165741 C1 | 4/2001 |
| RU | 2178681 C1 | 1/2002 |
| RU | 2179859 C1 | 2/2002 |
| RU | 2180539 C2 | 3/2002 |
| RU | 2185858 C1 | 7/2002 |
| WO | WO 95/12371 | 5/1995 |
| WO | WO 96/40033 | 12/1996 |
| WO | WO 97/37694 | 10/1997 |
| WO | WO 99/13779 | 3/1999 |
| WO | WO 00/19912 A | 4/2000 |
| WO | WO 00/29484 | 5/2000 |
| WO | WO 01/82937 A1 | 11/2001 |
| WO | WO 01/97826 A2 | 12/2001 |
| WO | WO 02/009591 A2 | 2/2002 |
| WO | WO 02/054998 A1 | 7/2002 |
| WO | WO 02/099591 A3 | 7/2002 |
| WO | WO 02/072128 A1 | 9/2002 |
| WO | WO 02/096302 | 12/2002 |
| WO | WO 03/002168 A1 | 1/2003 |

OTHER PUBLICATIONS

"Notification of Transmittal of the International Search Report or the Declaration", PCT/US2004/018885.

* cited by examiner

SYSTEM FOR CLOSING AN OPENING IN A BODY CAVITY

BACKGROUND OF THE INVENTION

The present invention relates to closing openings in a vessel or other body cavity. More specifically, the present invention relates to a closure device that quickly closes openings in body tissue by engaging the adventitia closely adjacent the wall of the vessel or body cavity.

There are a wide variety of procedures which require gaining internal access to blood vessels or other body cavities. Many such procedures also require the insertion of treatment devices into the blood vessel or body cavity. Many of these procedures utilize accessible arteries as entry points for the treatment devices. For example, some such arteries include the femoral artery or subclavian artery. There are also a wide variety of procedures which gain access to other body cavities in a minimally invasive fashion.

One problem which must be addressed during these procedures is how to seal or close the opening in the blood vessel or other body cavity once the treatment procedure has been completed. Some prior techniques include simply applying pressure to the opening until it seals itself sufficiently that the pressure may be released. However, this technique often requires that pressure must be consistently applied for an undesirable amount of time after the procedure. Similarly, this type of technique can require a patient's hospitalization to be extended until the treating physician is certain that the closure is complete.

Other techniques have involved suturing the wall of the vessel or body cavity itself. This has typically required the physician to peel back a rather large portion of the tissue surrounding the puncture in order to gain sufficient access to the blood vessel or body cavity that it may be sutured adequately. This can be an undesirably time consuming procedure, and it can result in significant discomfort to the patient.

Still other techniques have involved the insertion of embolic materials adjacent the puncture. Of course, this carries with it its own difficulties. For instances, it is desirable that the embolic material not be placed within a blood vessel or body cavity because this can result in an embolus forming within the blood vessel or body cavity. Similarly, however, it is desirable that the embolic material not be located to far proximal of the puncture because this can result in the blood vessel or body cavity bleeding into the interstitial space proximal of the opening in the blood vessel or body cavity, but distal to the embolic material.

Another problem associated with closing punctures in blood vessels is that during insertion and removal of various devices into the lumen of the blood vessel, the position of the vessel relative to the surface of the skin can change. Therefore, determining the exact position of the outer wall of the blood vessel can be difficult.

Similarly, when entry is gained into the lumen of the blood vessel by puncturing the blood vessel, the vessel may not have been punctured in a direction entirely orthogonal to the longitudinal axis of the blood vessel. Instead, the blood vessel may be punctured in a "side stick" fashion in which case the puncture is made in an off-center position. In such punctures, it is difficult to locate the outer wall of the blood vessel as well.

SUMMARY OF THE INVENTION

A closure device closes an opening in a body cavity. The closure device includes an elongate delivery member and a closure component which is removably connected to the distal end of the delivery member. The closure component has a collapsible backing movable between a non-collapsed position and a collapsed position. The closure component also includes a plurality of fibrous tissue engaging members disposed on the backing and oriented in a non-engaging orientation when traveling in a distal direction and in an engaging orientation when traveling in a proximal direction. The fibrous tissue engaging members become entangled in the backing when the backing is in the collapsed position.

The present invention can also include a method of closing an opening in a body. The method includes inserting distally through the opening a closure component having a collapsible pile backing with pile engaging hooks and tissue engaging hooks disposed thereon. The method further includes withdrawing the closure component proximally relative to the opening such that the tissue engaging hooks engage tissue adjacent the opening. The collapsible pile is then collapsed so that the pile engaging hooks engage portions of the pile backing.

DETAILED DESCRIPTION OF THE ILLUSTRATIVE EMBODIMENTS

Figure 1:
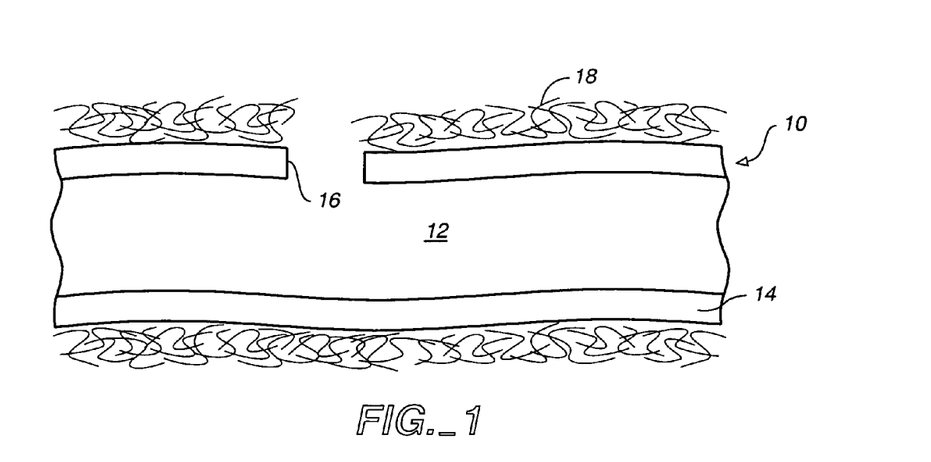
FIG. 1 is a side view of an opening in a blood vessel.

FIG. 1 is a side view of a portion of a blood vessel 10. While the present invention can be used with substantially any body cavity, a blood vessel is described herein for exemplary purposes only. Blood vessel 10 has a lumen 12 defined by a blood vessel wall 14. Blood vessel wall 14 is shown as having an opening 16 therein. Opening 16 can be an opening which was made, for example, in order to perform a treatment procedure during which access to lumen 12 is needed.

Vessel wall 14 is formed of media having an endothelial inner layer which is generally smooth muscular tissue. The media is surrounded by adventitia 18. As is known, the adventitia 18 includes fibrous collagen.

Figure 2:
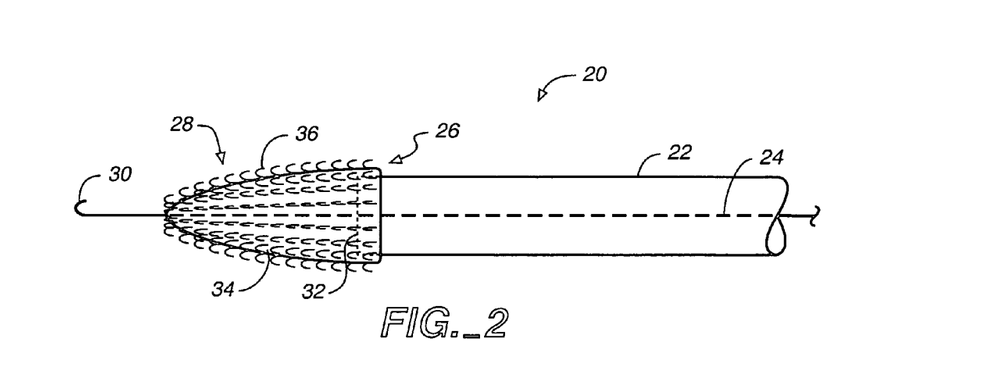
FIG. 2 is a side view of a portion of a closure device in accordance with one embodiment of the present invention.

FIG. 2 is a side view of a portion of a closure device 20 in accordance with one embodiment of the present invention. Closure device 20 includes an elongate member 22 which can be, for example, a catheter or wire having an inner lumen for receiving an optional wire 24. Elongate member 22 has a proximal end which is manipulable by the physician, and a distal end 26 which has closure member 28 mounted thereon.

Optional wire 24 is illustratively formed as a guide wire or core wire with a resilient hook 30 disposed at the distal end thereof. The functioning of hook 30 is described in greater detail below.

The distal end 26 of elongate member 22 illustratively includes a connection section 32 which is disconnectably connected to closure member 28. In one embodiment, closure member 28 includes a generally cone-shaped pile backing 34 with a plurality of hook members 36 disposed thereon. In one embodiment, the hooks 36 and pile 34 are formed from hook and loop fabric such as that sold under the commercial designation "VELCRO" or other similar material. In the embodiment in which closure member 28 is formed of hook and loop fabric, it is similar to conventional hook and loop fabric except that the hooks 36 of the hook and loop fabric are mounted on the loop or pile portion of the hook and loop fabric which forms backing 34. Therefore, if closure member 28 were to be compressed upon itself, it would stay in the compressed shape because the hooks 36 would engage the underlying loops which form backing 34.

Figure 3:
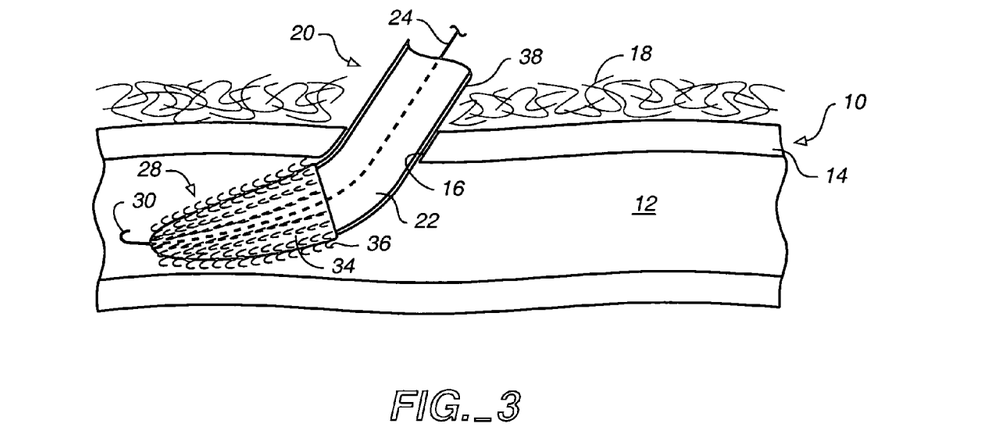
FIG. 3 illustrates the closure device shown in FIG. 2 inserted into the blood vessel shown in FIG. 1.

FIGS. 3-6 illustrate the operation of closure device 20 in accordance with one embodiment of the present invention, in which opening 16 in blood vessel 10 is closed using the device. FIG. 3 shows that an introducer sheath 38 has been introduced into opening 16 in blood vessel 10. Closure device 20 has been inserted through introducer sheath 38 into lumen 12. It should be noted, of course, that closure device 20 can be preloaded into the introducer sheath 38 before the introducer sheath is inserted into opening 16. Also, however, if introducer sheath 38 is already in place in the vessel 10 from some prior procedure, closure device 20 can simply be inserted through introducer sheath 38 after other devices have been removed therefrom.

In any case, it can be seen that hooks 26 are radially expanded and oriented such that, as they are advanced distally through the introducer sheath 38, they are in a non-engaging, or sliding, orientation. Hooks 36 may optionally be slightly collapsed toward the longitudinal central axis of the introducer sheath 38 as well, as they travel through the introducer sheath 38.

Once closure member 28 has emerged from the distal end of introducer sheath 38, the hooks 36, if they were compressed, assume their uncompressed position, in which they face proximally, as shown in FIG. 3. Therefore, hooks 36 are oriented on backing 34 such that they are in an engaging or hooking orientation as they move proximally.

Once closure member 28 has emerged from the distal end of introducer sheath 38, introducer sheath 38 is removed from opening 16 in blood vessel 10 by withdrawing it proximally. When that happens, the vessel wall 14 defining opening 16 contracts around elongate member 22.

Figure 4:
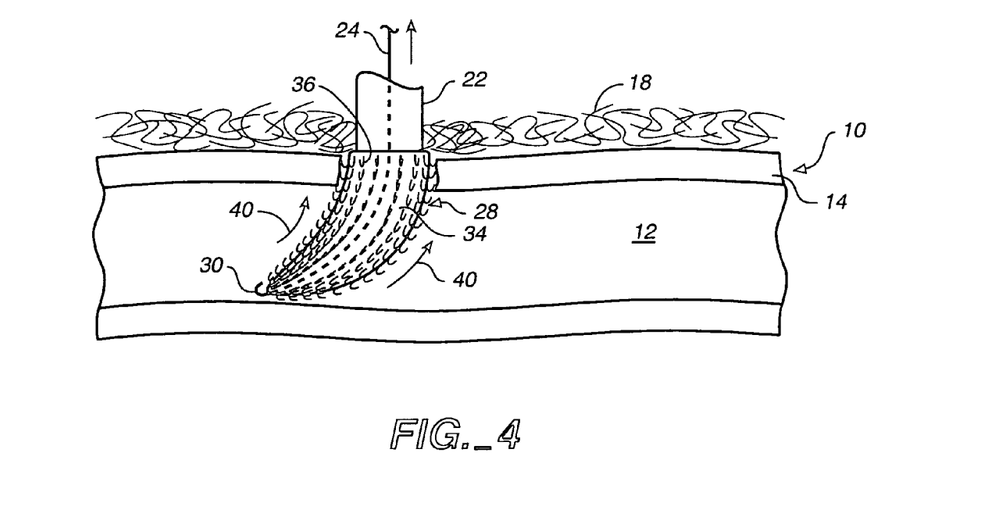
FIG. 4 illustrates partial closure of the opening in the blood vessel.

FIG. 4 shows closure device 26 in a position in which closure of opening 16 has begun. After introducer sheath 38 has been withdrawn proximally, elongate member 22 and wire 24 are also withdrawn proximally through opening 16. Hooks 36 travel through the media layer which forms vessel wall 14, without becoming tangled in that tissue, because it is rather smooth muscle tissue.

However, when elongate member 22 has been withdrawn proximally to a point where the first proximal row of hooks 36 encounter adventitia 18, that first row of hooks 36 quickly becomes entangled in the fibrous collagen adventitia tissue 18. Because the fibrous collagen is extremely strong, the first proximally located hooks 36 become very firmly entangled in adventitia 18. Thus, the physician can readily feel this simply by noting that further proximally withdrawal of elongate member 22 suddenly requires a great deal more force. When that occurs, the physician can either continue to withdraw elongate member 22, or stop withdrawing elongate member 22, temporarily, while the physician continues to withdraw wire 24 proximally.

As wire 24 is further withdrawn proximally, hook 30 on the distal end of wire 24 engages the distal tip of the backing material 34 and generally pulls the cone shaped backing material proximally with it in a direction indicated by arrows 40. Because the backing material is a flexible fabric, it begins to collapse on itself proximally. This exposes portions of the underlying fabric backing 34 to distally located hooks which are collapsing on top of it. Those hooks become firmly entangled in the backing, as is the case with conventional hook and loop fabric. The physician continues to withdraw wire 24 proximally continuing to cause closure member 28 to pile up on itself to form a closure.

Figure 5:
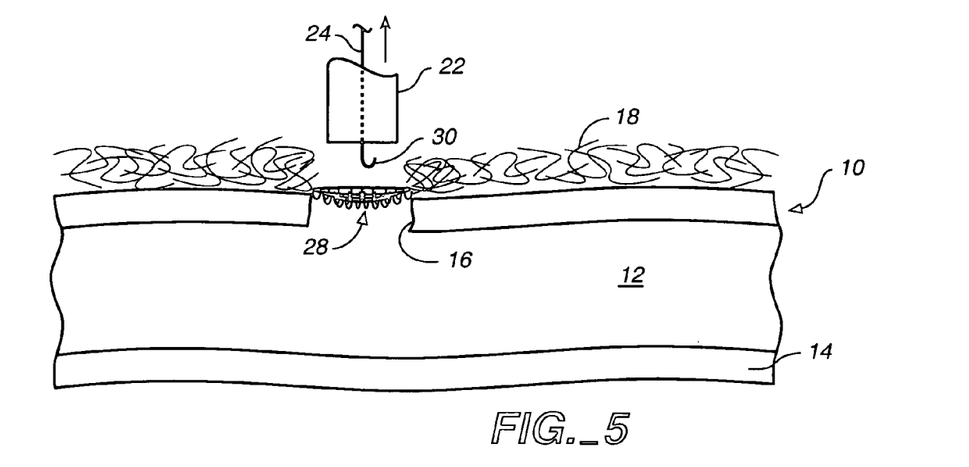
FIG. 5 illustrates a closure device in a fully collapsed position.

This is better illustrated with respect to FIG. 5. FIG. 5 shows that closure member 28 has piled upon itself and hooks 36 have engaged exposed portions of pile 34 to form a collapsed, snarled, closure of opening 16 wherein closure member 28 is also firmly entangled and anchored in adventitia 18.

As wire 24 is further withdrawn proximally, hook 30 deforms to pass through the distal opening in closure member 28 and to thus release closure member 28. The force required to deform hook 30 can be chosen, as desired, but is illustratively chosen to require a sufficient force to ensure that the closure device 28 has collapsed on itself a sufficient amount so it is fully withdrawn from the lumen 12 of vessel 10. Of course, other disconnection systems can be used as well, such as screw thread, a friction fit, a frangible mechanical connection, another hook and loop connection, or other suitable systems.

Proximally directed force is also exerted on elongate member 22 such that it disconnects from closure member 28. This disconnectable connection between the distal end of elongate member 22 and enclosure member 28 can be any suitable disconnectable connection, such as screw thread, a friction fit, an adhesive which can be disconnected through application of a desired amount of force, a frangible mechanical connection, another hook and loop connection in which a strip of loop fabric is disposed at the distal end of elongate member 22 and internal hooks, internal to closure member 28, are initially engaged in the loop fabric but are disengaged as elongate member 22 is withdrawn proximally, or any other suitable disconnectable connection.

Figure 6:
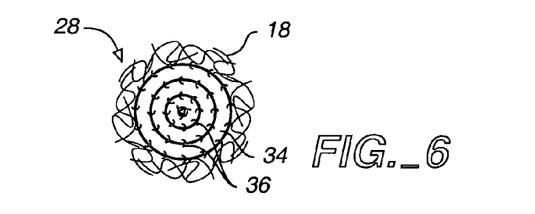
FIG. 6 is an end view of the closure device shown in FIG. 5.

FIG. 6 shows an end view of closure member 28 in the collapsed position, looking at closure member 28 from within the lumen 12 of vessel 10. As shown in FIG. 6, the hooks 36 of closure member 28 have engaged the exposed pile of backing 34. Also, the outer row of hooks 36 has engaged and become entangled in, adventitia 18, to form a substantially complete closure of opening 16 in the lumen 12 of vessel 10.

Figure 7A:
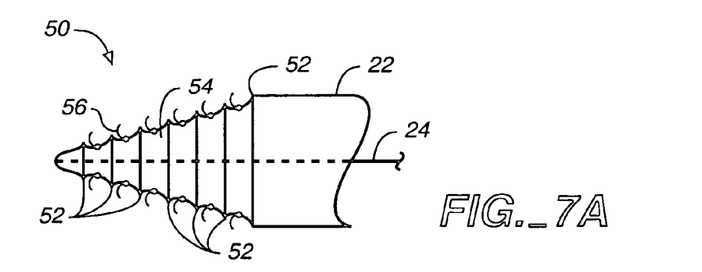
FIGS. 7A and 7B are side views of other embodiments of closure devices in accordance with the present invention.

FIG. 7A is a side view of another embodiment of a closure device 50. Closure device 50 is shown attached to elongate member 22 with wire 24 disposed therein. In FIG. 7A, device 50 is formed of a plurality of generally coaxially arranged rings 52. Rings 52 are progressively smaller the further they are located distally on device 50. Mounted between rings 52 is a web of material 54 which supports a plurality of hooks 56. As with hooks 36 shown in the earlier embodiment, hooks 56 are illustratively formed like the hooks in conventional hook and loop fabric. Rings 52 are structurally arranged such that, as wire 24 is withdrawn proximally, the distal tip of device 50 collapses onto the first distal ring 52. As force is continually exerted in the proximal direction on wire 24, each of the successive rings 52 collapses. Therefore, as with the first embodiment, device 50 is inserted into the lumen 12 of vessel 10. Elongate member 22 and wire 24 are then withdrawn proximally until the first proximal ring of hooks 56 engages the adventitia. Wire 24 is then drawn proximally (and elongate member 22 can be withdrawn proximally at this point as well) until each of the rings 52 has collapsed proximally to form a closure of opening 16 in vessel 10.

Figure 7B:
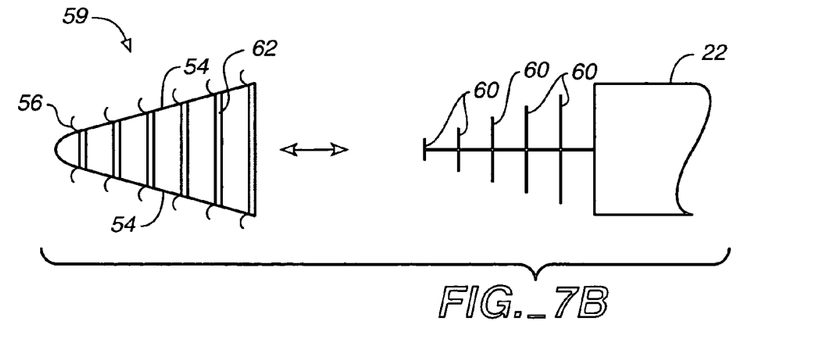

FIG. 7B illustrates another embodiment similar to that shown in FIG. 7A. However, FIG. 7B shows a closure device 59 in which elongate member 22 has disposed at its distal end a plurality of rings 60. Rows of hooks 56 are also mounted to a plurality of rings 62 which are disposed on web material 54. In the embodiment shown in FIG. 7B, web of material 54 is formed of a resilient, stretchable material. Rings 60 are formed slightly larger than the spaces between rings 62. Therefore, as web 54 is stretched over rings 60, rings 60 protrude outwardly stretching web 54 between rings 62, thereby holding closure device 59 in place on the distal end of the elongate member 52. Once web 54 is stretched over rings 60, device 59 takes substantially the same shape as that shown in FIG. 7A. However, for withdrawal, no wire 24 is needed. Instead, as elongate device 22 is withdrawn proximally, the first proximally located ring of hooks 56 on device 59 engages the adventitia. As additional proximal force is exerted on elongate member 22, the first proximal ring 60 becomes dislodged from within web 54. However, the remaining rings 60 are still frictionally engaged with the web 54 of device 59. As proximal force is continually exerted on elongate device 22, successive rows of hooks 56 are drawn proximally and engage the loops on web fabric 54, and successive rings 60 become dislodged from web 54. Thus, device 59 eventually collapses on itself proximally to again form a generally disc shaped closure device substantially closing the opening 16 in vessel 10, and being firmly anchored to the adventitia.

Of course, in the embodiment shown in FIGS. 7A and 7B, the entire web portions 54 can be covered with hooks 56, although not all hooks are shown for the sake of clarity.

Figure 8:
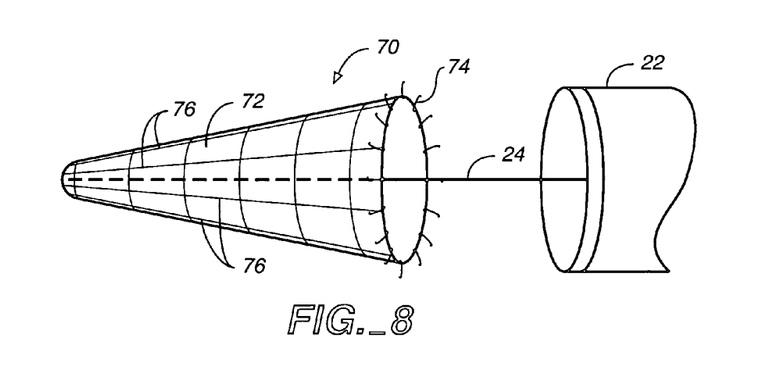
FIG. 8 is a side view of another embodiment of a closure device in accordance with the present invention.
Figure 9:
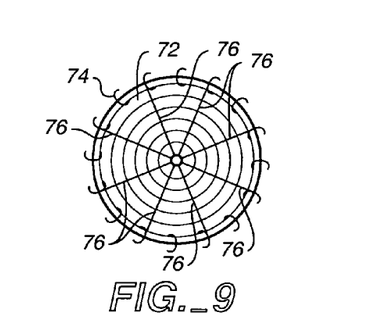
FIG. 9 is an end view of the closure device shown in FIG. 8 in a fully clasped position.

FIGS. 8 and 9 illustrate another embodiment of a closure device 70 in accordance with the present invention. Closure device 70 is again disconnectably connected to elongate member 22 and wire 24. Device 70 includes a web material 72 and a plurality of hooks 74. Again, the entire web 72 can be filled with hooks 74, although they are not shown simply for the sake of clarity. Web 72 is supported by collapsible structural members 76 which are either formed integrally with web 72 or connected thereto by a suitable connection technique. During operation, the first row of hooks 74 engages the adventitia and the user proximally withdraws wire 24. This causes the structural members supporting web 72 to collapse upon themselves, again forming a collapsed generally disc shaped closure such as that shown in FIG. 9.

Figure 10:
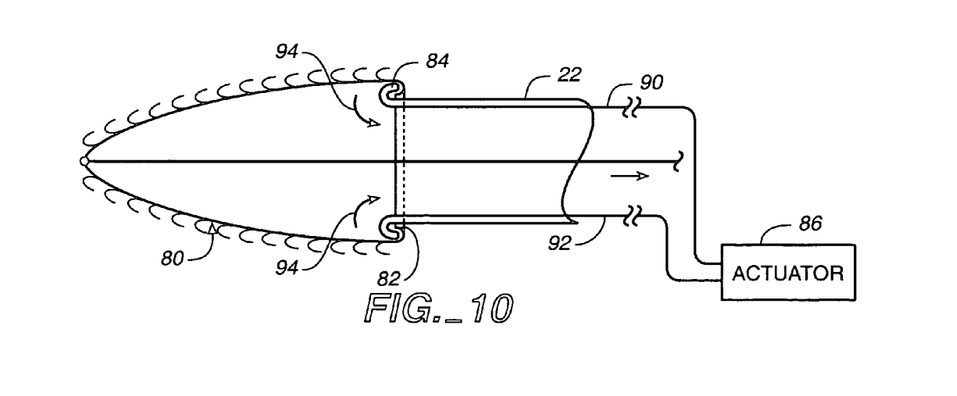
FIG. 10 is a side view of one embodiment of an actuable locking mechanism for locking a closure device on the distal end of an elongate member in accordance with one embodiment of the present invention.

FIG. 10 shows one embodiment of an actuable release mechanism. Instead of having a passive release mechanism, in which the user simply exerts force to release the closure tip from elongate member 22, FIG. 10 shows an actuation device for accomplishing the release. As shown in FIG. 10, a closure member 80 (which can be any of the described closure members) contains, at its proximal end, a hook-shaped lip 82. Also, FIG. 10 shows that, extending through elongate member 22 are a plurality of wires (or a sheath) which has mating hooks 84. Hooks 84 are connected to a proximal actuator 86 mechanism by linkages 90 and 92 which can simply be wires. Actuator 86 can be a trigger, a pull wire, a cylinder or any other desired actuable mechanism.

When actuator 86 is actuated, mating hooks 84 reciprocate generally in the direction indicated by arrows 94. Thus, hooks 84 come out of engagement with lip 82 and thus release mechanism 80.

For the embodiments discussed herein, the closure hooks and backing can be formed with any desired, known materials. For example, they can simply be biocompatible hook and loop fabric, or they can be bioabsorbable hook and loop fabric as well or other materials. Similarly, of course, they can be treated with any desired therapeutic agent to accomplish any desired effect, such as endothelial growth, drug release, antibiotics or any other desired therapeutic action.

In addition, it should be noted that while the hooks described herein can simply be hooks formed of conventional hook and loop fabric, they can also be formed of substantially rigid hooks with a sharpened, tissue piercing tip so that they can pierce tissue. In that embodiment, they can be used to close substantially any opening or traumatic wound in the skin. The sharpened hooks are located on the initial proximal rings of hooks for use in areas where no, or very little, adventitia is found. This allows the hooks to pierce other tissue, such as the skin. Subsequent collapse of the hook and pile fabric on itself, and release of the device, again closes the wound. Such a device can readily be used, for example, for emergency wound closure to close wounds quickly. During use, the device is simply inserted in the wound, and then withdrawn proximally. The sharpened hooks pierce and grab the skin, and the hook and pile collapses onto itself to form a closure, closing the wound.

Similarly, the hooks described herein are shown for purposes of clarity, as large hooks such as those used with conventional hook and loop fabric. However, they can of course be much smaller (such as microscopic) and formed of a wide variety of shapes, such as arrows, barbs, etc. Also, they could be randomly oriented and covered when inserted and exposed when withdrawn, so long as they are atraumic when traveling in the distal direction and engaging in the proximal direction.

Also, although the device has been shown as conical or round in shape the inventive aspects of the invention may be applied to virtually any anatomically required shape, including ovals, long strips or even a rolled up or other configuration. The protruding hook and pile structure may be a uniform or non-uniform shape to match the required anatomy.

It can thus be seen that the closure device discussed herein can accomplish closure of an opening in a vessel or body cavity by simply being inserted into the body cavity and then withdrawn in one smooth motion. The hooks become firmly entangled in the adventitia and therefore form a quick and reliable closure located at precisely the point where closure is desired.

Although the present invention has been described with reference to preferred embodiments, workers skilled in the art will recognize that changes may be made in form and detail without departing from the spirit and scope of the invention.

What is claimed is:

1. A closure device for closing an opening in a body cavity, comprising:

an elongate delivery member having a distal end and a proximal end;

a closure component removably connected to the distal end of the delivery member, the closure component including a collapsible backing movable between a non-collapsed delivery position, in which the backing tapers continuously from a proximal end to a distal end to form a generally conical shape with a center portion of the backing distally spaced from a periphery of the backing, and a collapsed deployed position, in which the backing center portion is collapsed proximally toward the backing periphery to have a generally disc shape, and a plurality of fibrous tissue engaging members disposed on the backing and oriented in a non-engaging orientation when traveling in a distal direction and in an engaging orientation when traveling in a proximal direction, the fibrous tissue engaging members entangling the backing when the backing is in the collapsed position; and a collapse actuator releasably coupled to the collapsible backing, the actuator having a detachable distal end that is received within a distal aperture in the closure component and extends distal to the distal aperture when the closure component is in the non-collapsed position, the collapse actuator being operable to move the collapsible backing from the non-collapsed position to the collapsed position, and wherein the detachable distal end of the collapse actuator is configured to assume a deformed profile solely in response to a sufficient proximal force applied to the collapse actuator, the deformed profile permitting the detachable distal end to pass proximally through the distal aperture and thereby detach from the collapsed closure component.

2. The closure device of claim 1 wherein the backing is formed in a generally elongate conformation, along a generally longitudinal axis of the backing, in the non-collapsed position.

3. The closure device of claim 2 wherein the backing is collapsed generally along the longitudinal axis thereof when in the collapsed position.

4. The closure device of claim 3 wherein the fibrous tissue engaging members form proximally facing hooks.

5. The closure device of claim 4 wherein the proximally facing hooks are spaced along the backing from a proximal portion thereof to a distal portion thereof when the backing is in the non-collapsed position.

6. The closure device of claim 5 wherein the hooks entangle in the backing located proximal of the hooks as the backing moves from the non-collapsed position to the collapsed position.

7. The closure device of claim 4 wherein the body cavity is defined by generally smooth tissue and has fibrous tissue proximal thereof and wherein at least a subset of the plurality of hooks are oriented to engage the fibrous tissue as the hooks travel in a proximal direction relative to the fibrous tissue.

8. The closure device of claim 7 wherein the closure component has a first row of hooks disposed about the backing periphery.

9. The closure device of claim 8 wherein the first row of hooks passes along the generally smooth tissue without engaging the generally smooth tissue and engages the fibrous tissue as the closure component is moved proximally relative thereto.

10. The closure device of claim 4 wherein the closure component has a first row of hooks disposed about a proximal end thereof and wherein the first row of hooks includes tissue piercing hooks that pierce tissue as they are moved proximally relative thereto.

11. The closure device of claim 1 and further comprising:
an active actuator having a distal engaging end disconnectably connecting the closure component to the delivery member and a proximal end receiving an actuation input and actuating the distal engaging end to release the closure component in response to the actuation input.

12. The closure device of claim 1 wherein the detachable distal end of the collapse actuator is releasably coupled to a distal end of the closure component and is configured to move the distal end of the closure component under proximally directed force applied to the elongate member.

13. The closure device of claim 12 in which the detachable distal end of the collapse actuator includes a deformable hook for releasably coupling the collapse actuator to the closure component.

14. The closure device of claim 13 wherein the deformable hook is located distal of the distal aperture when the closure component is in the non-collapsed position.

15. The closure device of claim 14 wherein the deformable hook moves from a distal end of the closure component to a more proximal position to collapse the closure component under proximally directed force applied to the collapse actuator.

16. The closure device of claim 15 wherein the deformable hook deforms to pass through the distal aperture in the closure component after the closure component has moved to the collapsed position under continued application of proximally directed force on the collapse actuator.

17. The closure device of claim 12 wherein the collapse actuator comprises a wire.

18. The closure device of claim 17 wherein the wire comprises a frangible connection to the distal end of the closure component.

19. The closure device of claim 17 wherein the wire comprises a mechanically releasable connection to the distal end of the closure component.

20. The closure device of claim 1 wherein the closure component is formed of a biocompatible material.

21. The closure device of claim 1 wherein the closure component is formed of a bioabsorbable material.

22. The closure device of claim 1 wherein the fibrous tissue engaging members and the backing are disposed on a same surface of the closure component.

23. The closure device of claim 22 wherein the same surface comprises an exterior surface of the closure component.

24. A method of closing an opening in a body, comprising:
inserting distally through the opening a closure component having collapsible pile backing with pile engaging hooks and tissue engaging hooks disposed thereon, the pile backing initially have a non-collapsed delivery position in which the backing tapers continuously from a proximal end to a distal end to form a generally conical shape with a center portion of the backing distally spaced from a periphery of the backing;

withdrawing the closure component proximally relative to the opening such that the tissue engaging hooks engage tissue adjacent the opening;

applying proximally directed force to a collapse actuator releasably coupled to the collapsible pile backing and having a detachable distal end received within a distal aperture of the collapsible pile backing, the detachable distal end extending distal to the distal aperture, thereby to collapse the collapsible pile backing to a collapsed position in which the backing center portion is moved proximally toward the backing periphery to form a generally disc shape, and wherein the pile engaging hooks engage portions of the pile backing to retain the pile backing in the collapsed position; and disconnecting the collapse actuator from the collapsible pile backing by applying additional proximally directed force on the collapse actuator, thereby causing the detachable distal end of the collapse actuator to assume a deformed profile solely in response to a sufficient proximal force applied to the collapse actuator, the deformed profile permitting the detachable distal end to pass proximally through the distal aperture and the collapsed pile backing.

25. The method of claim 24 wherein inserting comprises:
inserting the closure component with an elongate delivery member, the closure component being disposed at a distal end of the delivery member.

26. The method of claim 25 and further comprising:
disconnecting the closure component from the distal end of the delivery member.

27. The method of claim 26 wherein disconnecting comprises:
exerting proximally directed force on the delivery member after collapsing the collapsible pile.

28. The method of claim 24 wherein the tissue engaging hooks are comprised of tissue piercing hooks that pierce the tissue when the tissue is engaged.

29. The method of claim 24 wherein the opening is in a body cavity defined by media and having adventitia adjacent thereto and wherein withdrawing comprises:
withdrawing the tissue engaging hooks proximally past the media to engage the adventitia.

30. A closure device for closing an opening in a body cavity, comprising:
an elongate delivery member having a distal end and a proximal end;
an implantable closure component disconnectably connected to the distal end of the delivery member, the closure component including a longitudinally collapsible backing movable between a non-collapsed delivery position, in which the backing tapers continuously from a proximal end to a distal end to form a generally conical shape with a center portion of the backing distally spaced from a periphery of the backing, and a collapsed deployed position, in which the backing center portion is collapsed proximally toward the backing periphery to have a generally disc shape, and a plurality of fibrous tissue engaging members on the backing and engaging the backing when the backing is in the collapsed position; and
a collapse actuator releasably coupled to the collapsible backing, the actuator having a detachable distal end that is received within a distal aperture in the closure component and extends distal to the distal aperture when the closure component is in the non-collapsed position, the collapse actuator being operable to move the collapsible backing from the non-collapsed position to the collapsed position, and wherein the detachable distal end of the collapse actuator is configured to assume a deformed profile solely in response to a sufficient proximal force applied to the collapse actuator, the deformed profile permitting the detachable distal end to pass proximally through the distal aperture and thereby detach from the collapsed closure component.

31. The closure device of claim 30 wherein the fibrous tissue engaging members are oriented in a non-engaging orientation when traveling in a distal direction and in an engaging orientation when traveling in a proximal direction.

32. The closure device of claim 30 wherein the backing is formed in a generally elongate conformation, along a generally longitudinal axis of the backing, in the non-collapsed position.

33. The closure device of claim 30 wherein the fibrous tissue engaging members form proximally facing hooks.

34. The closure device of claim 33 wherein the proximally facing hooks are spaced along the backing from a proximal portion thereof to a distal portion thereof when the backing is in the non-collapsed position.

35. The closure device of claim 34 wherein the hooks entangle in the backing located proximal of the hooks as the backing moves from the non-collapsed position to the collapsed position.

36. The closure device of claim 35 wherein the body cavity is defined by generally smooth tissue and has fibrous tissue proximal thereof and wherein at least a subset of the plurality of hooks are oriented to engage the fibrous tissue as the hooks travel in a proximal direction relative to the fibrous tissue.

* * * * *